(12) United States Patent
Gough et al.

(10) Patent No.: US 8,734,439 B2
(45) Date of Patent: May 27, 2014

(54) ABLATION APPARATUS AND METHOD

(75) Inventors: Edward J. Gough, Menlo Park, CA (US); Alan A. Stein, Moss Beach, CA (US); Stuart D. Edwards, Corral de Tierra, CA (US)

(73) Assignee: AngioDynamics, Inc, Latham, NY (US)

( * ) Notice: Subject to any disclaimer, the term of this patent is extended or adjusted under 35 U.S.C. 154(b) by 1357 days.

(21) Appl. No.: 12/041,709

(22) Filed: Mar. 4, 2008

(65) Prior Publication Data

US 2008/0154259 A1 Jun. 26, 2008

Related U.S. Application Data

(63) Continuation of application No. 10/775,747, filed on Feb. 9, 2004, which is a continuation of application No. 08/577,208, filed on Dec. 22, 1995, now Pat. No. 6,689,127, which is a continuation-in-part of application No. 08/515,379, filed on Aug. 15, 1995, now Pat. No. 5,683,384, application No. 12/041,709, which is a continuation of application No. 11/016,384, filed on Dec. 17, 2004, which is a continuation of application No. 08/963,239, filed on Nov. 3, 1997, now Pat. No. 6,958,062, which is a continuation-in-part of application No. 08/605,323, filed on Feb. 14, 1996, now Pat. No. 5,728,143, which is a continuation-in-part of application No. 08/515,379, filed on Aug. 15, 1995, now Pat. No. 5,683,384.

(51) Int. Cl.
*A61B 18/14* (2006.01)

(52) U.S. Cl.
USPC ............................................. 606/41; 607/102

(58) Field of Classification Search
USPC ........... 606/41, 42, 45–50; 607/101, 102, 116
See application file for complete search history.

(56) References Cited

U.S. PATENT DOCUMENTS

| | | | |
|---|---|---|---|
| 3,474,777 | A | 10/1969 | Figge et al. |
| 3,834,392 | A | 9/1974 | Lampman et al. |
| 3,858,586 | A | 1/1975 | Lessen |
| 3,987,795 | A | 10/1976 | Morrison, Jr. |
| 3,991,770 | A | 11/1976 | LeVeen |
| 4,011,872 | A | 3/1977 | Komiya |
| 4,016,881 | A | 4/1977 | Rioux et al. |
| 4,016,886 | A | 4/1977 | Doss |
| 4,026,301 | A | 5/1977 | Friedman et al. |
| 4,033,351 | A | 7/1977 | Hetzel |
| 4,043,342 | A | 8/1977 | Morrison, Jr. |
| 4,074,718 | A | 2/1978 | Morrison, Jr. |
| 4,080,959 | A | 3/1978 | LeVeen |

(Continued)

FOREIGN PATENT DOCUMENTS

| | | |
|---|---|---|
| DE | 10 07 960 | 10/1957 |
| DE | 21 24 684 | 11/1972 |

(Continued)

*Primary Examiner* — Michael Peffley
(74) *Attorney, Agent, or Firm* — Peter J. Flora

(57) ABSTRACT

An ablation apparatus includes an ablation energy source producing an electromagnetic energy output. A multiple antenna device is included, and has a primary antenna with a longitudinal axis, a central lumen and a distal end, and a secondary antenna with a distal end. The secondary antenna is deployed from the primary antenna central lumen in a lateral direction relative to the longitudinal axis. The multiple antenna device is coupled to the ablation energy source.

24 Claims, 9 Drawing Sheets

(56) References Cited

U.S. PATENT DOCUMENTS

| | | |
|---|---|---|
| 4,085,756 A | 4/1978 | Weaver |
| 4,095,602 A | 6/1978 | LeVeen |
| 4,119,102 A | 10/1978 | LeVeen |
| 4,121,592 A | 10/1978 | Whalley |
| 4,140,130 A | 2/1979 | Storm, III |
| 4,154,246 A | 5/1979 | LeVeen |
| 4,230,129 A | 10/1980 | LeVeen |
| 4,237,898 A | 12/1980 | Whalley |
| 4,269,174 A | 5/1981 | Adair |
| 4,285,346 A | 8/1981 | Armitage |
| 4,289,135 A | 9/1981 | Nordenstrom et al. |
| 4,290,435 A | 9/1981 | Waggott |
| 4,303,636 A | 12/1981 | Gordon |
| 4,331,654 A | 5/1982 | Morris |
| 4,337,760 A | 7/1982 | Rubin |
| 4,345,588 A | 8/1982 | Widder et al. |
| 4,346,715 A | 8/1982 | Gammell |
| 4,375,220 A | 3/1983 | Matvias |
| 4,409,993 A | 10/1983 | Furihata |
| 4,411,266 A | 10/1983 | Cosman |
| 4,418,692 A | 12/1983 | Guay |
| 4,461,283 A | 7/1984 | Doi |
| 4,506,680 A | 3/1985 | Stokes |
| 4,512,762 A | 4/1985 | Spears |
| 4,524,770 A | 6/1985 | Orandi |
| 4,532,924 A | 8/1985 | Auth et al. |
| 4,545,368 A | 10/1985 | Rand et al. |
| RE32,057 E | 12/1985 | LeVeen |
| RE32,066 E | 1/1986 | LeVeen |
| 4,562,838 A | 1/1986 | Walker |
| 4,565,200 A | 1/1986 | Cosman |
| 4,574,782 A | 3/1986 | Borrelli et al. |
| 4,583,556 A | 4/1986 | Hines et al. |
| 4,586,490 A | 5/1986 | Katz |
| 4,601,296 A | 7/1986 | Yerushalmi |
| 4,648,892 A | 3/1987 | Kittrell et al. |
| 4,652,257 A | 3/1987 | Chang |
| 4,658,819 A | 4/1987 | Harris et al. |
| 4,660,571 A | 4/1987 | Hess et al. |
| 4,662,359 A | 5/1987 | Gordon |
| 4,676,258 A | 6/1987 | Inokuchi et al. |
| 4,690,130 A | 9/1987 | Mirell |
| 4,692,139 A | 9/1987 | Stiles |
| 4,709,701 A | 12/1987 | Weber |
| 4,753,248 A | 6/1988 | Engler et al. |
| 4,763,671 A | 8/1988 | Goffinet |
| 4,776,086 A | 10/1988 | Kasevich et al. |
| 4,800,899 A | 1/1989 | Elliott |
| 4,813,429 A | 3/1989 | Eshel et al. |
| 4,818,542 A | 4/1989 | Deluca et al. |
| 4,823,791 A | 4/1989 | D'Amelio et al. |
| 4,823,793 A | 4/1989 | Angulo et al. |
| 4,825,880 A | 5/1989 | Stauffer et al. |
| 4,838,265 A | 6/1989 | Cosman et al. |
| 4,846,196 A | 7/1989 | Wiksell et al. |
| 4,860,744 A | 8/1989 | Johnson et al. |
| 4,862,887 A | 9/1989 | Weber et al. |
| 4,881,543 A | 11/1989 | Trembly et al. |
| 4,887,614 A | 12/1989 | Shirakami et al. |
| 4,907,589 A | 3/1990 | Cosman |
| 4,920,978 A | 5/1990 | Colvin |
| 4,931,047 A | 6/1990 | Broadwin et al. |
| 4,940,064 A | 7/1990 | Desai |
| 4,945,912 A | 8/1990 | Langberg |
| 4,947,842 A | 8/1990 | Marchosky et al. |
| 4,950,267 A | 8/1990 | Ishihara et al. |
| 4,962,761 A | 10/1990 | Golden |
| 4,963,364 A | 10/1990 | Fox et al. |
| 4,966,604 A | 10/1990 | Reiss |
| 4,976,680 A | 12/1990 | Hayman et al. |
| 4,976,711 A | 12/1990 | Parins et al. |
| 4,983,159 A | 1/1991 | Rand |
| 4,985,022 A | 1/1991 | Fearnot et al. |
| 4,989,601 A | 2/1991 | Marchosky et al. |
| 5,003,991 A | 4/1991 | Takayama et al. |
| 5,007,908 A | 4/1991 | Rydell |
| 5,009,656 A | 4/1991 | Reimels |
| 5,010,897 A | 4/1991 | LeVeen |
| 5,011,483 A | 4/1991 | Sleister |
| 5,013,312 A | 5/1991 | Parins et al. |
| 5,015,227 A | 5/1991 | Broadwin et al. |
| 5,016,615 A | 5/1991 | Driller et al. |
| 5,026,959 A | 6/1991 | Ito et al. |
| 5,047,027 A | 9/1991 | Rydell |
| 5,055,100 A | 10/1991 | Olsen |
| 5,057,107 A | 10/1991 | Parins et al. |
| 5,059,199 A | 10/1991 | Okada et al. |
| 5,067,952 A | 11/1991 | Gudov et al. |
| 5,071,419 A | 12/1991 | Rydell et al. |
| 5,078,717 A | 1/1992 | Parins et al. |
| 5,080,660 A | 1/1992 | Buelna |
| 5,083,565 A | 1/1992 | Parins |
| 5,084,001 A | 1/1992 | Van't Hooft et al. |
| 5,084,045 A | 1/1992 | Helenowski |
| 5,085,659 A | 2/1992 | Rydell |
| 5,099,756 A | 3/1992 | Franconi et al. |
| 5,100,423 A | 3/1992 | Fearnot |
| 5,115,818 A | 5/1992 | Holleman et al. |
| 5,119,832 A | 6/1992 | Xavier |
| 5,122,137 A | 6/1992 | Lennox |
| 5,125,928 A | 6/1992 | Parins et al. |
| 5,128,147 A | 7/1992 | LeVeen et al. |
| RE34,086 E | 10/1992 | George |
| 5,156,151 A | 10/1992 | Imran |
| 5,167,626 A | 12/1992 | Casper et al. |
| 5,169,396 A | 12/1992 | Dowlatshahi et al. |
| 5,170,789 A | 12/1992 | Narayan et al. |
| 5,170,805 A | 12/1992 | Kensey et al. |
| 5,178,620 A | 1/1993 | Eggers et al. |
| 5,183,455 A | 2/1993 | Hayman et al. |
| 5,190,517 A | 3/1993 | Zieve et al. |
| 5,190,539 A | 3/1993 | Fletcher et al. |
| 5,190,541 A | 3/1993 | Abele |
| 5,190,766 A | 3/1993 | Ishihara |
| 5,197,466 A | 3/1993 | Marchosky et al. |
| 5,197,963 A | 3/1993 | Parins |
| 5,197,964 A | 3/1993 | Parins |
| 5,203,353 A | 4/1993 | Easley et al. |
| 5,203,782 A | 4/1993 | Gudov et al. |
| 5,205,289 A | 4/1993 | Hardy et al. |
| 5,207,675 A | 5/1993 | Canady |
| 5,215,103 A | 6/1993 | Desai |
| 5,217,458 A | 6/1993 | Parins |
| 5,222,953 A | 6/1993 | Dowlatshahi |
| 5,236,410 A | 8/1993 | Granov et al. |
| 5,236,424 A | 8/1993 | Imran |
| 5,246,438 A | 9/1993 | Langberg |
| 5,249,585 A | 10/1993 | Turner et al. |
| 5,251,645 A | 10/1993 | Fenn |
| 5,252,922 A | 10/1993 | Larson, III |
| 5,257,451 A | 11/1993 | Edwards et al. |
| 5,258,006 A | 11/1993 | Rydell et al. |
| 5,259,394 A | 11/1993 | Bens |
| 5,259,395 A | 11/1993 | Li |
| 5,267,994 A | 12/1993 | Gentelia et al. |
| 5,273,535 A | 12/1993 | Edwards et al. |
| 5,275,162 A | 1/1994 | Edwards et al. |
| 5,277,696 A | 1/1994 | Hagen |
| 5,281,213 A | 1/1994 | Milder et al. |
| 5,281,217 A | 1/1994 | Edwards et al. |
| 5,281,218 A | 1/1994 | Imran |
| 5,282,797 A | 2/1994 | Chess |
| 5,286,253 A | 2/1994 | Fucci |
| 5,290,286 A | 3/1994 | Parins |
| 5,293,869 A | 3/1994 | Edwards et al. |
| 5,295,955 A | 3/1994 | Rosen et al. |
| 5,300,068 A | 4/1994 | Rosar et al. |
| 5,300,069 A | 4/1994 | Hunsberger et al. |
| 5,300,099 A | 4/1994 | Rudie |
| 5,304,214 A | 4/1994 | DeFord et al. |
| 5,309,910 A | 5/1994 | Edwards et al. |
| 5,313,943 A | 5/1994 | Houser et al. |
| 5,314,466 A | 5/1994 | Stern et al. |
| 5,322,503 A | 6/1994 | Desai |

(56) References Cited

U.S. PATENT DOCUMENTS

| | | | |
|---|---|---|---|
| 5,328,467 | A | 7/1994 | Edwards et al. |
| 5,334,193 | A | 8/1994 | Nardella |
| 5,334,206 | A | 8/1994 | Daikuzono |
| 5,336,222 | A | 8/1994 | Durgin, Jr. et al. |
| 5,342,357 | A | 8/1994 | Nardella |
| 5,348,554 | A | 9/1994 | Imran et al. |
| 5,354,296 | A | 10/1994 | Turkel |
| 5,363,861 | A | 11/1994 | Edwards et al. |
| 5,365,926 | A | 11/1994 | Desai |
| 5,366,490 | A | 11/1994 | Edwards et al. |
| 5,368,592 | A | 11/1994 | Stern et al. |
| 5,370,675 | A * | 12/1994 | Edwards et al. .............. 607/101 |
| 5,370,678 | A | 12/1994 | Edwards et al. |
| 5,383,876 | A | 1/1995 | Nardella |
| 5,383,917 | A | 1/1995 | Desai et al. |
| 5,385,544 | A | 1/1995 | Edwards et al. |
| 5,397,339 | A | 3/1995 | Desai |
| 5,398,683 | A | 3/1995 | Edwards et al. |
| 5,401,272 | A | 3/1995 | Perkins |
| 5,403,311 | A | 4/1995 | Abele et al. |
| 5,405,346 | A | 4/1995 | Grundy et al. |
| 5,409,453 | A | 4/1995 | Lundquist et al. |
| 5,411,025 | A | 5/1995 | Webster, Jr. |
| 5,417,687 | A | 5/1995 | Nardella |
| 5,421,819 | A | 6/1995 | Edwards et al. |
| 5,423,807 | A | 6/1995 | Milder |
| 5,423,808 | A | 6/1995 | Edwards et al. |
| 5,423,811 | A | 6/1995 | Imran et al. |
| 5,433,708 | A | 7/1995 | Nichols et al. |
| 5,435,805 | A | 7/1995 | Edwards et al. |
| 5,437,662 | A | 8/1995 | Nardella |
| 5,437,664 | A | 8/1995 | Cohen et al. |
| 5,456,662 | A | 10/1995 | Edwards et al. |
| 5,456,682 | A | 10/1995 | Edwards et al. |
| 5,458,596 | A | 10/1995 | Lax et al. |
| 5,458,597 | A * | 10/1995 | Edwards et al. ................ 606/41 |
| 5,462,521 | A | 10/1995 | Brucker et al. |
| 5,470,308 | A | 11/1995 | Edwards et al. |
| 5,470,309 | A | 11/1995 | Edwards et al. |
| 5,471,982 | A | 12/1995 | Edwards et al. |
| 5,472,441 | A * | 12/1995 | Edwards et al. ................ 606/41 |
| 5,484,400 | A | 1/1996 | Edwards et al. |
| 5,486,161 | A | 1/1996 | Lax et al. |
| 5,500,012 | A | 3/1996 | Brucker et al. |
| 5,505,730 | A | 4/1996 | Edwards |
| 5,507,743 | A * | 4/1996 | Edwards et al. ................ 606/41 |
| 5,509,419 | A | 4/1996 | Edwards et al. |
| 5,514,130 | A | 5/1996 | Baker |
| 5,514,131 | A | 5/1996 | Edwards |
| 5,520,684 | A | 5/1996 | Imran |
| 5,531,676 | A | 7/1996 | Edwards et al. |
| 5,531,677 | A | 7/1996 | Lundquist et al. |
| 5,536,240 | A | 7/1996 | Edwards et al. |
| 5,536,267 | A | 7/1996 | Edwards et al. |
| 5,540,655 | A | 7/1996 | Edwards et al. |
| 5,542,915 | A | 8/1996 | Edwards et al. |
| 5,542,916 | A | 8/1996 | Hirsch et al. |
| 5,542,928 | A | 8/1996 | Evans et al. |
| 5,545,161 | A | 8/1996 | Imran |
| 5,545,171 | A | 8/1996 | Sharkey et al. |
| 5,545,193 | A | 8/1996 | Fleischman et al. |
| 5,546,267 | A | 8/1996 | Frederiksen et al. |
| 5,549,108 | A | 8/1996 | Edwards et al. |
| 5,549,644 | A | 8/1996 | Lundquist et al. |
| 5,554,110 | A | 9/1996 | Edwards et al. |
| 5,556,377 | A | 9/1996 | Rosen et al. |
| 5,558,672 | A | 9/1996 | Edwards et al. |
| 5,558,673 | A | 9/1996 | Edwards et al. |
| 5,560,358 | A | 10/1996 | Arnold et al. |
| 5,562,703 | A | 10/1996 | Desai |
| 5,599,345 | A | 2/1997 | Edwards et al. |
| 5,599,346 | A | 2/1997 | Edwards et al. |
| 5,609,151 | A | 3/1997 | Mulier et al. |
| 5,620,481 | A | 4/1997 | Desai et al. |
| 5,685,839 | A | 11/1997 | Edwards et al. |
| 5,817,092 | A | 10/1998 | Behl |
| 5,827,276 | A * | 10/1998 | LeVeen et al. .................. 606/41 |
| 5,868,740 | A | 2/1999 | LeVeen et al. |
| 6,009,877 | A * | 1/2000 | Edwards ....................... 128/898 |

FOREIGN PATENT DOCUMENTS

| | | |
|---|---|---|
| DE | 41 00 422 | 10/1992 |
| DE | 38 38 840 | 2/1997 |
| DE | 39 30 451 | 9/2002 |
| EP | 0 462 302 | 12/1991 |
| EP | 0 502 268 | 9/1992 |
| EP | 0 519 415 | 12/1992 |
| EP | 0472 368 | 6/1995 |
| EP | 0 370 890 | 11/1995 |
| EP | 0 566 430 | 3/1997 |
| EP | 0 608 609 | 9/2001 |
| FR | 2 283 701 | 4/1976 |
| FR | 2 670 664 | 6/1992 |
| JP | 63-275632 | 11/1988 |
| JP | 2-121675 | 5/1990 |
| WO | WO 92/10142 | 6/1992 |
| WO | WO 94/04220 | 3/1994 |
| WO | WO 94/10925 | 5/1994 |
| WO | WO 94/11059 | 5/1994 |
| WO | WO 94/17856 | 8/1994 |
| WO | WO 94/25110 | 11/1994 |
| WO | WO 94/26178 | 11/1994 |
| WO | WO 95/19142 | 7/1995 |
| WO | WO 95/25471 | 10/1995 |
| WO | WO 96/04860 | 2/1996 |
| WO | WO 96/29946 | 10/1996 |
| WO | WO 97/06739 | 5/1998 |
| WO | WO 97/06855 | 8/1998 |

* cited by examiner

ABLATION APPARATUS AND METHOD

CROSS-REFERENCE TO RELATED APPLICATIONS

This application is a continuation of U.S. application Ser. No. 10/775,747, filed Feb. 9, 2004, which is a continuation of U.S. application Ser. No. 08/577,208, filed Dec. 22, 1995, now U.S. Pat. No. 6,689,127, which is a continuation-in-part of U.S. application Ser. No. 08/515,379, filed Aug. 15, 1995, now U.S. Pat. No. 5,683,384; and this application is a continuation of U.S. application Ser. No. 11/016,384, filed Dec. 17, 2004, which is a continuation of U.S. application Ser. No. 08/963,239, filed Nov. 3, 1997, now U.S. Pat. No. 6,958,062, which is a continuation-in-part of U.S. application Ser. No. 08/605,323, filed Feb. 14, 1996, now U.S. Pat. No. 5,728,143, which is a continuation-in-part of U.S. application Ser. No. 08/515,379, filed Aug. 15, 1995, now U.S. Pat. No. 5,683,384; all of these related applications and patents are incorporated herein in their entirety by express reference thereto.

FIELD OF THE ART

This application relates generally to a treatment and ablation apparatus that includes an introducer inserted into or adjacent to a selected body mass, such as a tumor, with one or more deployed secondary antennas, and more particularly to a multiple antenna RF treatment and ablation apparatus. This application further relates generally to a multiple antenna ablation apparatus, and more particularly to a multiple antenna ablation apparatus where the size of the antennas' electromagnetic energy delivery surfaces is sufficient to prevent the apparatus from impeding out. This application further relates to a treatment apparatus that includes one or multiple deployable members for anchoring and/or treatment, and tissue treatment methods that deploy, advance, and/or retract the one or multiple deployable members. Methods to ablate a selected tissue mass may include introducing the introducer into the selected mass, deploying a distal end of the secondary antenna into the selected mass, and applying electromagnetic energy to the secondary antenna.

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective treatment are not completely understood. However, four cellular effects of hyperthermia on cancerous tissue have been proposed: (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA, and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

During RF treatment, a high frequency alternating current flows from the electrode into the tissue. Ionic agitation is produced in the region of tissue about the electrode as the ions attempt to follow the directional variations of the alternating current. This agitation results in frictional heating so that the tissue about the electrode, rather than the electrode itself, is the primary source of heat. Tissue heat generated is produced by the flow of current through the electrical resistance offered by the tissue. The greater this resistance, the greater the heat generated.

Current spreads out radially from the electrode, so that current density is greatest next to the electrode, and decreases progressively at distances from it. The frictional heat produced from ionic agitation is proportional to current density. Therefore, the heating effect is greatest next to the electrode and decreases with distance from it. If the current density is too high, the tissue temperature next to the electrode rapidly exceeds desired levels and carbonization and boiling occurs in a thin tissue shell surrounding the electrode. One consequence of this is that lesions can inadvertently be made smaller than anticipated for a given electrode size. There must be time for equilibrium heating of tissue to be reached, especially at the center of the desired lesion volume.

SUMMARY

This application provides tissue treatment device which includes multiple antennas. The treatment device may include an introducer that pierces and advances through tissue, a secondary electrode positioned in an introducer lumen that is laterally deployable from the introducer into a selected tissue mass. The secondary electrode may be electromagnetically coupled to an electromagnetic energy source. The introducer may be electromagnetically coupled to an electromagnetic energy source. One or more of the introducer and the electrode, or the distal portions thereof, may include a treatment delivery surface. One or more of the introducer and the electrode, or the distal portions thereof, may include one or more treatment delivery apertures. One or more of the introducer and the electrode may include one or more lumens. The treatment device may be configured for delivery of one or more treatments, such as being a multi-modality apparatus.

This application further provides a method for tissue treatment. The method may include: providing an introducer that includes one or more deployable means including at least one anchoring means; positioning a distal portion of the introducer within or adjacent to a selected tissue mass; deploying the at least one anchoring means from the introducer to anchor the introducer relative to the selected tissue mass; delivering one or more treatments through at least one of the deployable means to treat a first volume of tissue; advancing the at least one deployable means further to a position within or adjacent to the selected tissue mass; and delivering one or more treatments through the at least one deployable means at the position to treat a second volume of tissue.

Another tissue treatment method may include: providing an introducer that includes one or more deployable means including at least one anchoring means; positioning a distal portion of the introducer within or adjacent to a selected tissue mass; deploying the at least one anchoring means from the introducer to anchor the introducer relative to the selected tissue mass; and delivering one or more treatments through at least one of the introducer and the deployable means to treat a volume of tissue.

A further tissue treatment method may include: providing an introducer that includes one or more deployable means; positioning a distal portion of the introducer within or adjacent to a selected tissue mass; deploying at least one of the deployable means from the introducer to a first position within or adjacent to the selected tissue mass; delivering one or more treatments through the at least one deployable means at the first position to treat a first volume of tissue; advancing the at least one deployable means further to a second position within or adjacent to the selected tissue mass; and delivering one or more treatments through the at least one deployable means at the second position to treat a second volume of tissue.

A further tissue treatment method may include: providing an introducer that comprises one or more deployable means; positioning a distal portion of the introducer within or adjacent to a selected tissue mass; delivering one or more treatments to at least one of the deployable means; and deploying the at least one deployable means from the introducer and advancing the at least one deployable means further to create a series of treatment volumes within or adjacent to the selected tissue mass.

The tissue treatment methods may further include retracing the one or more anchoring and/or treatment means back to the introducer. The tissue treatment methods may further include delivering the one or more treatments through one or more delivery surfaces of the introducer and/or at least one anchoring and/or treatment means, or through one or more lumens of the introducer and/or at least one anchoring and/or treatment means, or both. The tissue treatment methods may further include delivering the one or more treatments through one or more delivery surfaces of the introducer and/or at least one anchoring and/or treatment means, and adjusting the size or length of the one or more delivery surfaces. The tissue treatment methods may further include changing the one or more treatments between a monopolar mode and a bipolar mode. The tissue treatment methods may further include delivering the one or more treatments in bipolar mode between the multiple treatment means, or delivering the one or more treatments in bipolar mode between the introducer and at least one of treatment means, or both.

The one or more treatments delivered during the tissue treatment methods may include one or more of energy (e.g., radiofrequency), therapeutic agents, conductivity enhancement mediums, tissue ablation, or infusion. The one or more treatments may result in one or more of: (i) changes in cell or nuclear membrane permeability or fluidity, (ii) cytoplasmic lysomal disintegration, (iii) protein thermal damage, and (iv) potential excitation of immunologic systems.

One or more of the deployable means may be anchoring and/or treatment means. One or more of the deployable means may be configured to detect impedance and/or temperature. One or more sensors may be positioned at an interior or exterior of the introducer and/or the deployable means. A control system may be coupled to the sensors. The control system may include a multiplexer. The feedback control system may include a temperature detection circuit. The control system may modify the duration of the one or more treatments, adjust the one or more treatments, or cut off the delivery of the one or more treatments to achieve the desired level of treatment (e.g., achieve desired ablation without impeding out, minimize the ablation of non-targeted tissue). An insulation sleeve may be positioned around the introducer. The introducer and the one or more of the deployable means can be operated in monopolar or bipolar modes, and may be capable of switching between the two.

DETAILED DESCRIPTION

The present application provides an ablation treatment apparatus which includes an ablation energy source producing an electromagnetic energy output. A multiple antenna device is included and has a primary antenna with a longitudinal axis, a central lumen and a distal end, and a secondary antenna with a distal end. The secondary antenna is deployable from the primary antenna central lumen in a lateral direction relative to the longitudinal axis. The primary antenna and the secondary antennas are each electromagnetically coupled to the electromagnetic energy source.

Figure 1:
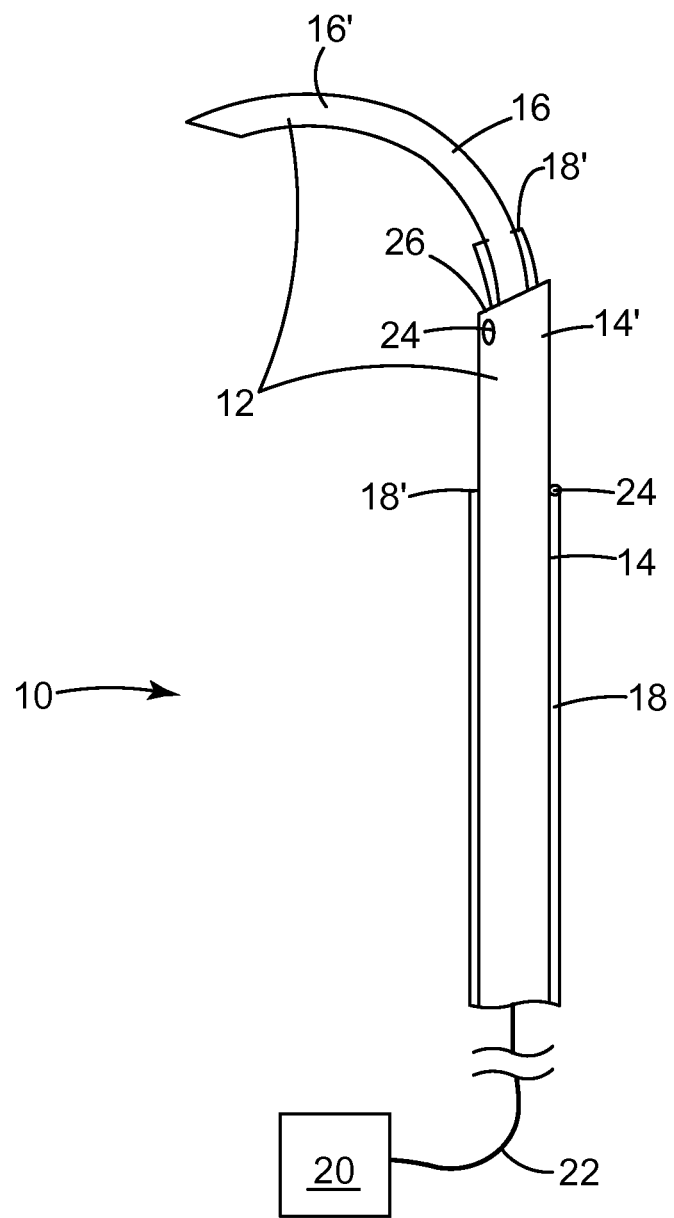
FIG. 1 is a perspective view of a multiple antenna ablation apparatus, illustrating a primary antenna and a single laterally deployed secondary antenna.

As shown in FIG. 1, an ablation treatment apparatus 10 includes a multiple antenna device 12. Multiple antenna device 12 includes a primary antenna 14, and one or more secondary antennas 16, which are typically electrodes. Secondary antennas 16 are initially positioned in a primary antenna lumen when primary antenna 14 is advanced through tissue. When primary antenna 14 reaches a selected tissue ablation site in a selected tissue mass, including but not limited to a solid lesion, secondary antennas 16 are laterally deployed from the primary antenna lumen and into the selected tissue mass. Ablation proceeds from the interior of the selected tissue mass in a direction towards a periphery of the selected tissue mass.

Each of the primary and secondary antennas 14 and 16 has an exterior ablation surface which delivers electromagnetic energy to the selected tissue mass. The length and size of each ablation surface can be variable. The length of primary antenna ablation surface relative to secondary antenna ablation surface can be 20% or greater, 33 and ⅓% or greater, 50% or greater, 75% or greater, about the same length, or greater than the length of secondary electrode ablation surface. Lengths of primary and secondary antennas 14 and 16 can be adjustable. Primary antenna 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. The ablation can be between the ablation surfaces of primary and secondary antennas 14 and 16 when operated in a mono-polar mode with a ground pad.

Primary antenna 14 is constructed so that it can be introduced percutaneously or laparoscopically through tissue without an introducer. Primary antenna 14 combines the function of an introducer and an electrode.

In one embodiment, primary antenna 14 can have a sharpened distal end 14' to assist introduction through tissue. Each secondary antenna 16 has a distal end 16' that is constructed to be less structurally rigid than primary antenna 14. Distal end 16' is that section of secondary antenna 16 that is advanced from the lumen of primary antenna 14 and into the selected tissue mass. Distal end 16' is typically less structurally rigid than primary antenna 14. However, sections of secondary antenna 16 which are not advanced through the selected tissue mass may be less structurally rigid than primary antenna 14.

Structural rigidity difference between primary antenna 14 and distal end 16' of secondary antenna 16 is achieved by: (i) choosing different materials for antenna 14 and for distal end 16' or for some greater length of secondary antenna 16, (ii) using the same material but having less of it for secondary antenna 16 or distal end 16', e.g., secondary antenna 16 or distal end 16' is not as thick as primary antenna 14, or (iii) including another material in one of the antennas 14 or 16 to vary their structural rigidity. For purposes of this disclosure, structural rigidity is defined as the amount of deflection that an antenna has relative to its longitudinal axis. It will be appreciated that a given antenna will have different levels of rigidity depending on its length.

Primary and secondary antennas 14 and 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of primary or secondary antennas 14 or 16 can have different lengths. The lengths can be determined by the actual physical length of an antenna, the amount of an antenna that has an ablation delivery surface, and the length of an antenna that is not covered by an insulator. The actual length of an antenna depends on the location of the selected tissue mass to be ablated, its distance from the skin, its accessibility as well as whether or not the physician chooses a laparoscopic, percutaneous or other procedure. Further, ablation treatment apparatus 10, and more particularly multiple antenna device 12, can be introduced through a guide to the desired tissue mass site.

An insulation sleeve 18 may be positioned around an exterior of one or both of the primary and secondary antennas 14 and 16. Each insulation sleeve 18 is adjustably positioned so that the length of an antenna ablation surface can be varied. Each insulation sleeve 18 surrounding a primary antenna 14 can include one or more apertures. This permits the introduction of a secondary antenna 16 through primary antenna 14 and insulation sleeve 18.

In one embodiment, insulation sleeve 18 can comprise a polyamide material. A sensor 24 may be positioned on top of insulation sleeve 18. The insulation sleeve 18 is semi-rigid. Sensor 24 can be laid down substantially along the entire length of insulation sleeve 18. Primary antenna 14 is made of a stainless-steel hypodermic tubing with 2 cm of exposed ablation surface. Secondary antennas 16 have distal ends 16' that are made of NiTi hypodermic tubing. A handle is included with markings to show the varying distance of secondary antennas 16 from primary antenna 14. Fluid infusion is delivered through a Luer port at a side of the handle. Type-T thermocouples are positioned at distal ends 16'.

An energy source 20 is connected to multiple antenna device 12 with one or more cables 22. Energy source 20 can be an RF source, microwave source, short wave source, laser source and the like. Multiple antenna device 12 can be comprised of primary and secondary antennas 14 and 16 that are RF electrodes, microwave antennas, as well as combinations thereof. Energy source 20 may be a combination RF/microwave box. Further a laser optical fiber, coupled to a laser source 20 can be introduced through one or both of primary and secondary antennas 14 and 16. One or more of the primary and secondary antennas 14 and 16 can be an arm for the purposes of introducing the optical fiber.

Antennas 14 and 16 are each electromagnetically coupled to energy source 20. The coupling can be direct from energy source 20 to each antenna 14 and 16, or indirect by using a collet, sleeve, and the like which couples antennas 14 and 16 to energy source 20.

One or more sensors 24 may be positioned on at least a portion of interior or exterior surfaces of primary antenna 14, secondary antenna 16, or insulation sleeve 18. Sensors 24 are positioned at primary antenna distal end 14', secondary antenna distal end 16' and insulation sleeve distal end 18'. Sensors 24 permit accurate measurement of temperature at a tissue site in order to determine: (i) the extent of ablation, (ii) the amount of ablation, (iii) whether or not further ablation is needed, and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include T type thermocouples with copper-constantan, J type thermocouples, E type thermocouples, K type thermocouples, fiber optics, resistive wires, thermocouple IR detectors, and the like. It will be appreciated that sensors 24 need not be thermal sensors.

Sensors 24 may measure temperature and/or impedance to permit monitoring a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at energy source 20 which then regulates the amount of energy delivered to primary and/or secondary antennas 14 and 16.

Thus the geometry of the ablated mass is selectable and controllable. Any number of different ablation geometries can be achieved. This is a result of having variable lengths for primary antenna 14 and secondary antenna 16 ablation surfaces as well as the inclusion of sensors. 24.

Distal end 16' of secondary antenna 16 is laterally deployed relative to a longitudinal axis of primary antenna 14 out of an aperture 26 formed in primary antenna 14. Aperture 26 is at distal end 14', or formed in a side of an exterior, of antenna 14.

Figure 2:
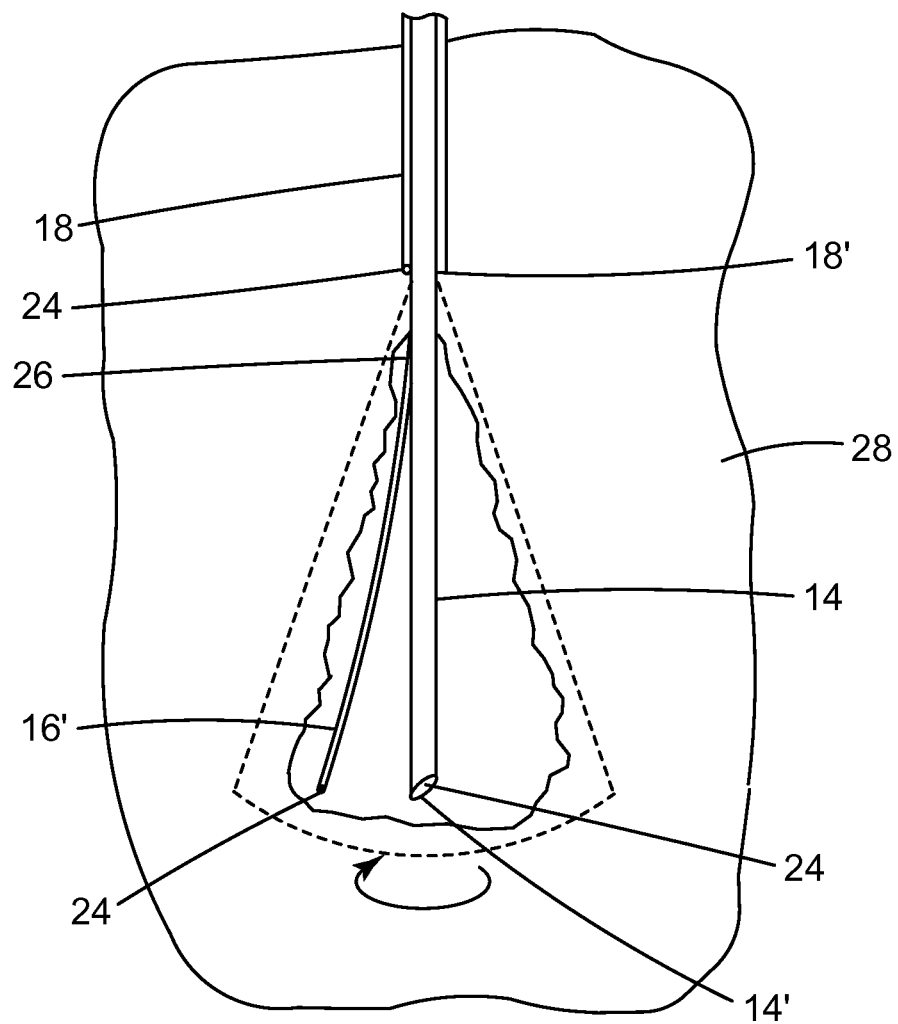
FIG. 2 is a perspective view of a conic geometric ablation achieved with the apparatus of FIG. 1.

As illustrated in FIG. 2, primary antenna 14 has been introduced into a selected tissue mass 28. One or more secondary antennas 16 are positioned within a primary antenna lumen as primary antenna 14 is introduced into and through the selected tissue mass 28. Subsequently, secondary antenna distal end 16' is advanced out of aperture 26 and into selected tissue mass 28. Insulation sleeves 18 are adjusted for primary and secondary antennas 14 and 16, respectively. RF, microwave, short wave, laser, and the like energy is delivered to antenna 16 in a monopolar mode (RF), or alternatively, multiple antenna device 12 can be operated in a bipolar mode (RF). Multiple antenna device 12 can be switched between monopolar and bipolar operation and have multiplexing capability between antennas 14 and 16. Secondary antenna distal end 16' is retracted back into primary antenna 14, and primary antenna 14 is then rotated. Secondary antenna distal end 16' is then introduced into selected tissue mass 28. Secondary antennas 16 may be introduced a short distance into selected tissue mass 28 to ablate a small area. Secondary antennas 16 can then be advanced further into selected tissue mass 28 any number of times to create more ablation zones. Secondary antenna distal end 16' is retracted back into primary antenna 14, and primary antenna 14 can be: (i) rotated again, (ii) moved along a longitudinal axis of selected tissue mass 28 to begin another series of ablations, or (iii) removed from selected tissue mass 28. A number of parameters permit ablation of selected tissue masses 28 of different sizes and shapes, including a series of ablations having primary and secondary antennas 14 and 16 with variable length ablation surfaces and the use of sensors 24.

In one embodiment, a method for creating an ablation volume in a selected tissue mass 28 includes providing an ablation device 12 with a primary antenna 14 with a distal end 14', a secondary antenna 16 with a distal end 16', and an energy source (not shown) coupled to both antennas 14 and 16. A ground pad electrode (not shown) is also included. The primary antenna 14 is inserted into the selected tissue mass 28 with distal end 16' of secondary antenna 16 positioned in a lumen of primary antenna 14. Distal end 16' of secondary antenna 16 is advanced out of the primary antenna lumen into the selected tissue mass 28 in a lateral direction relative to a longitudinal axis of the primary antenna 14. Electromagnetic energy is delivered through one of: a primary antenna ablation surface, a secondary antenna ablation surface, or both, to the selected tissue mass 28. This creates an ablation volume in the selected tissue mass 28.

There is wide variation in the amount of deflection of secondary antenna 16. For example, secondary antenna 16 can be deflected a few degrees from the longitudinal axis of primary antenna 14, or secondary antenna can be deflected in any number of geometric configurations, including but not limited to a "J" hook. Further, secondary antenna 16 is capable of being introduced from primary antenna 14 a few millimeters from primary antenna, or a much larger distance. Ablation by secondary antenna 16 can begin a few millimeters away from primary antenna 14, or secondary electrode 16 can be advanced a greater distance from primary antenna 14 and at that point the initial ablation by secondary antenna 16 begins.

A number of parameters permit ablation of selected tissue masses (including, but not limited to, tumors of different sizes and shapes), including a series of ablations having primary and secondary antennas 14 and 16 with variable length ablation surfaces, the use of sensors 24 and the use of a feedback control system.

Figure 3:
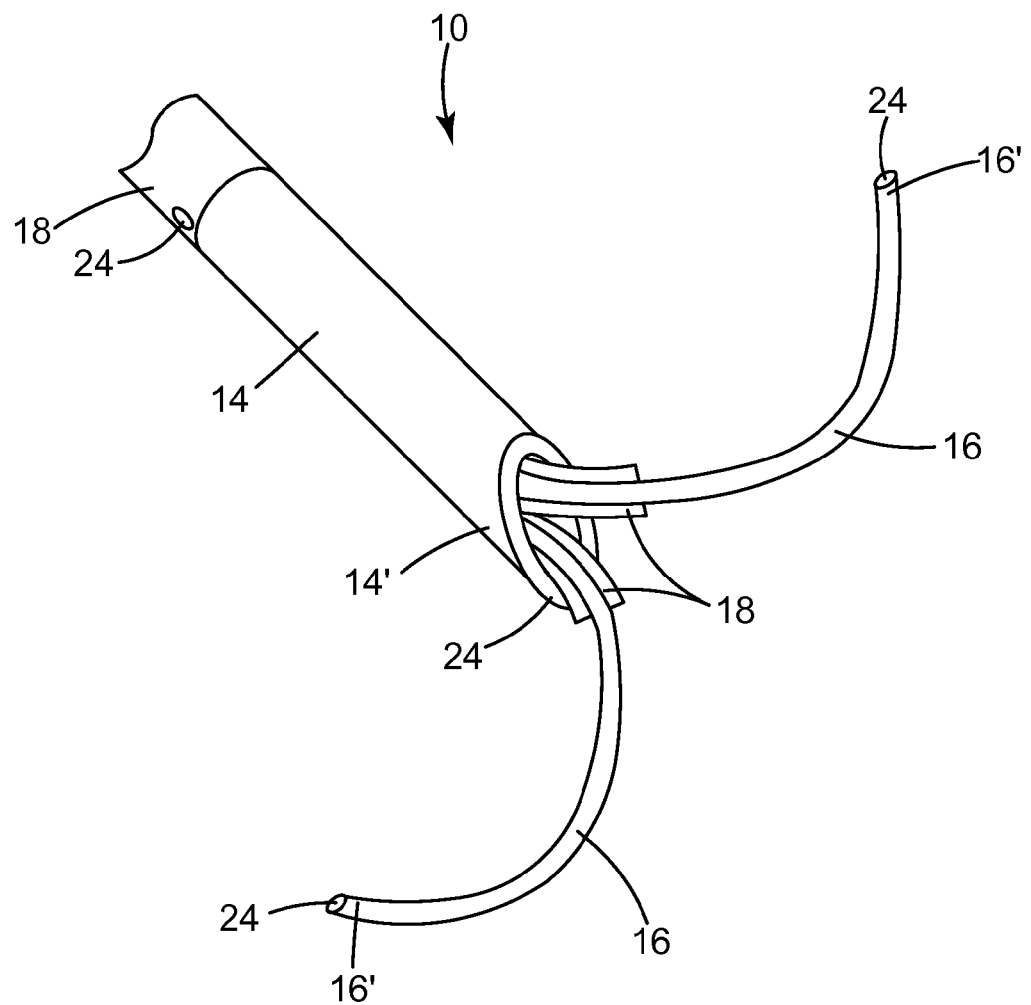
FIG. 3 is a perspective view of a multiple antenna ablation apparatus with two secondary antennas.

In FIG. 3, two secondary antennas 16 are each deployed out of distal end 14' of primary antenna 14 and introduced into a selected tissue mass. Secondary antennas 16 form a plane, and the area of ablation extends between the ablation surfaces of primary and secondary antennas 14 and 16. Primary antenna 14 can be introduced in an adjacent relationship to selected tissue mass. This particular deployment is particularly useful for small selected tissue masses, or where piercing selected tissue mass is not desirable. Primary antenna 14 can be rotated, with secondary antennas 16 retracted into a central lumen of primary antenna 14. Then the two secondary antennas 16 are deployed out of primary antenna 14, and another ablation volume defined between the two secondary antennas 16 is created. Further, primary electrode 14 can be withdrawn from its initial position adjacent to selected tissue mass, repositioned to another position adjacent to selected tissue mass, and secondary antennas 16 deployed to begin another ablation cycle. Any variety of different positionings may be utilized to create a desired ablation geometry for selected tissue masses of different geometries and sizes.

Figure 4:
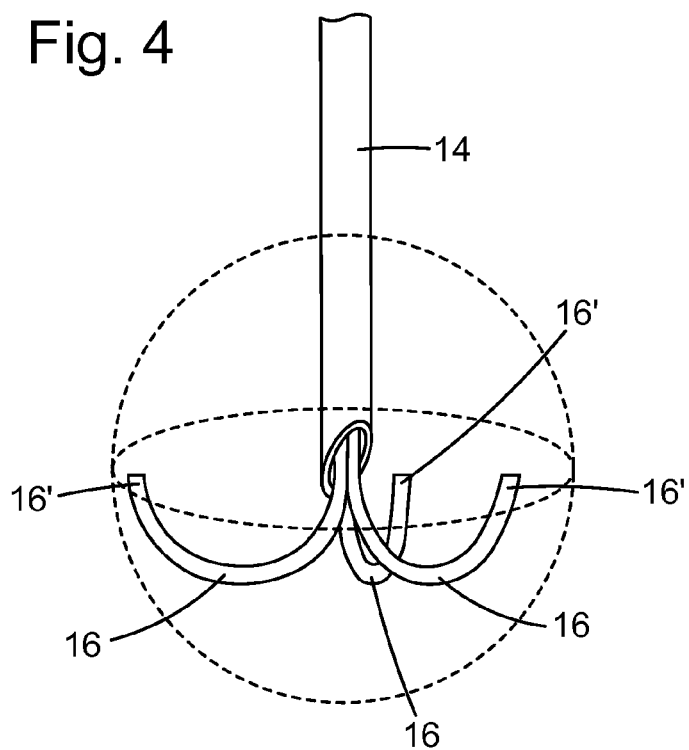
FIG. 4 is a perspective view illustrating the adjacent positioning of a multiple antenna ablation apparatus next to a selected tissue mass.

In FIG. 4, three secondary antennas 16 are introduced into a selected tissue mass. The effect is the creation of an ablation volume without leaving non-ablated areas between antenna ablation surfaces. The ablation is complete.

Figure 5:
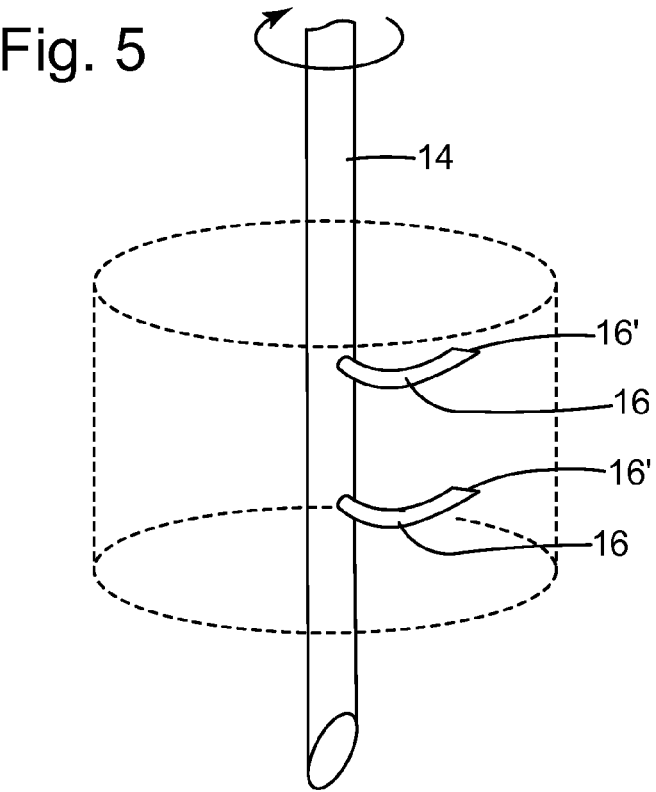
FIG. 5 is a perspective view illustrating the positioning of a multiple antenna ablation apparatus in the center of a selected tissue mass, and the creation of a cylindrical ablation.

Referring now to FIG. 5, a center of a selected tissue mass is pierced by primary antenna 14, secondary antennas 16 are laterally deployed and retracted, primary antenna 14 is rotated, secondary antennas 16 are deployed and retracted, and so on until a cylindrical ablation volume is achieved. A multiple antenna device containing antennas 14 and 16 can be operated in the bipolar mode between the two secondary antennas 16, or between a secondary antenna 16 and primary antenna 14. Alternatively, a multiple antenna device containing antennas 14 and 16 can be operated in a monopolar mode.

Figure 6A:
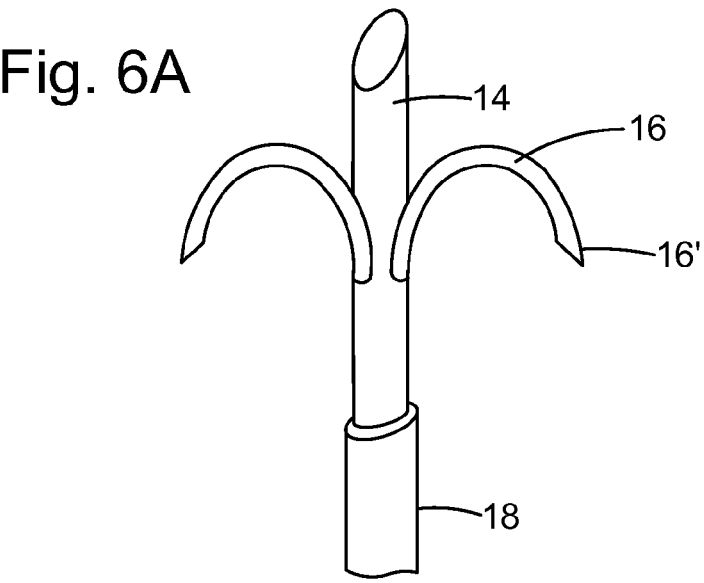
FIG. 6A is a perspective view of a multiple antenna ablation apparatus illustrating two secondary antennas which provide a retaining and anchoring function.
Figure 6B:
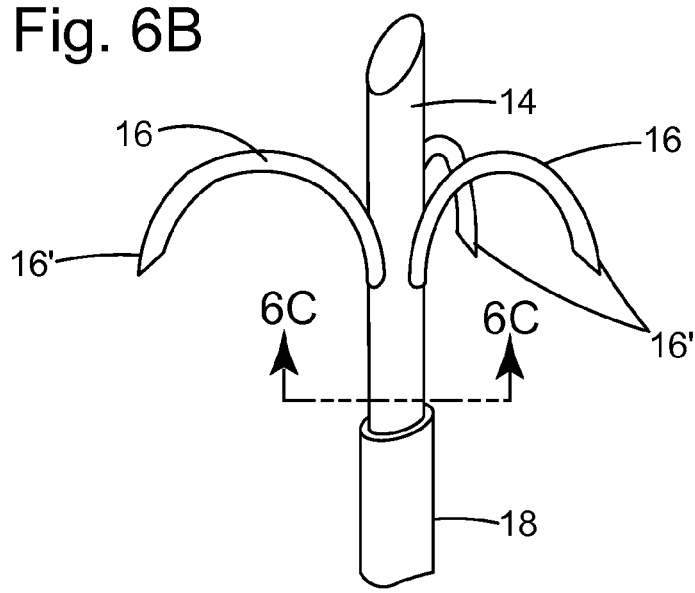
FIG. 6B is a perspective view of a multiple antenna ablation apparatus illustrating three secondary antennas which provide a retaining and anchoring function.

Secondary antennas 16 can serve the additional function of anchoring a multiple antenna device in a selected mass, as illustrated in FIGS. 6A and 6B. In FIG. 6A, one or both secondary antennas 16 are used to anchor and position primary antenna 14. Further, one or both secondary antennas 16 are also used to ablate tissue. In FIG. 6B, three secondary antennas 16 are deployed to anchor primary antenna 14.

Figure 6C:
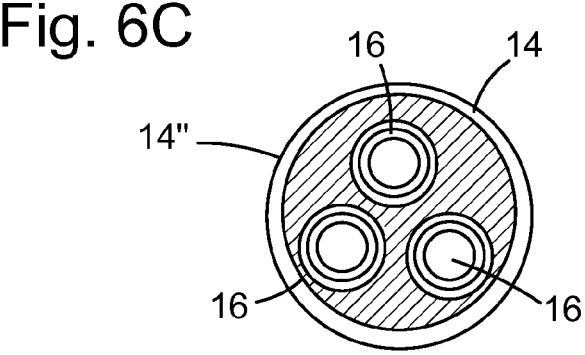
FIG. 6C is a cross-sectional view of the apparatus of FIG. 6(b) taken along the lines 6(c)-6(c).

FIG. 6C illustrates the infusion capability of a multiple antenna device. Three secondary antennas 16 are positioned in a central lumen 14" of primary antenna 14. One or more of the secondary antennas 16 can also include a central lumen coupled to an infusion source. Central lumen 14" is coupled to an infusion source and delivers a variety of infusion mediums to selected places both within and outside of the targeted ablation mass. Suitable infusion mediums include, but are not limited to, therapeutic agents, conductivity enhancement mediums, contrast agents or dyes, and the like. An example of a therapeutic agent is a chemotherapeutic agent.

Figure 7:
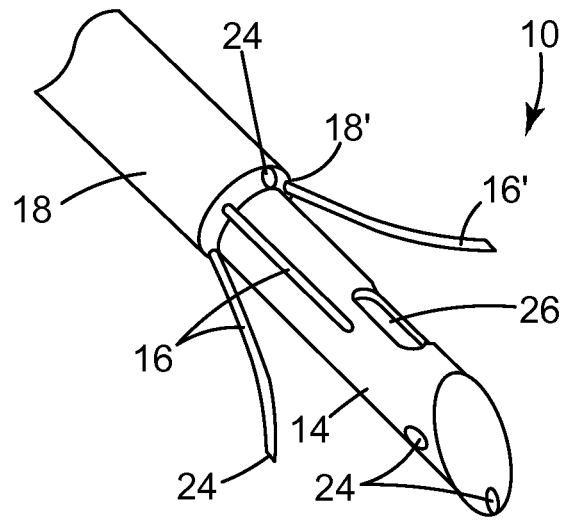
FIG. 7 is a perspective view of a multiple antenna ablation apparatus illustrating the deployment of three secondary antennas from a distal end of the insulation sleeve surrounding the primary antenna.
Figure 8:
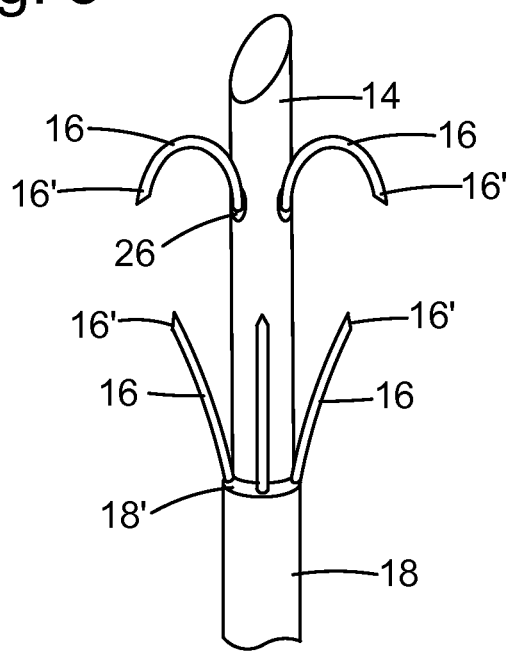
FIG. 8 is a perspective view of a multiple antenna ablation apparatus illustrating the deployment of two secondary antennas from the primary antenna, and the deployment of three secondary antennas from the distal end of the insulation sleeve surrounding the primary antenna.

As shown in FIG. 7, insulation sleeve 18 can include one or more lumens for receiving secondary antennas 16 which are deployed out of a distal end 18' of insulation sleeve 18. FIG. 8 illustrates three secondary antennas 16 being introduced out of distal end 18' of insulation sleeve, and two secondary antennas 16 being introduced through apertures 26 formed in primary antenna 14. As illustrated, the secondary electrodes 16 introduced through apertures 26 provide an anchoring function. It will be appreciated that FIG. 8 illustrates how secondary antennas 16 can have a variety of different geometric configurations in a multiple antenna device.

Figure 9:
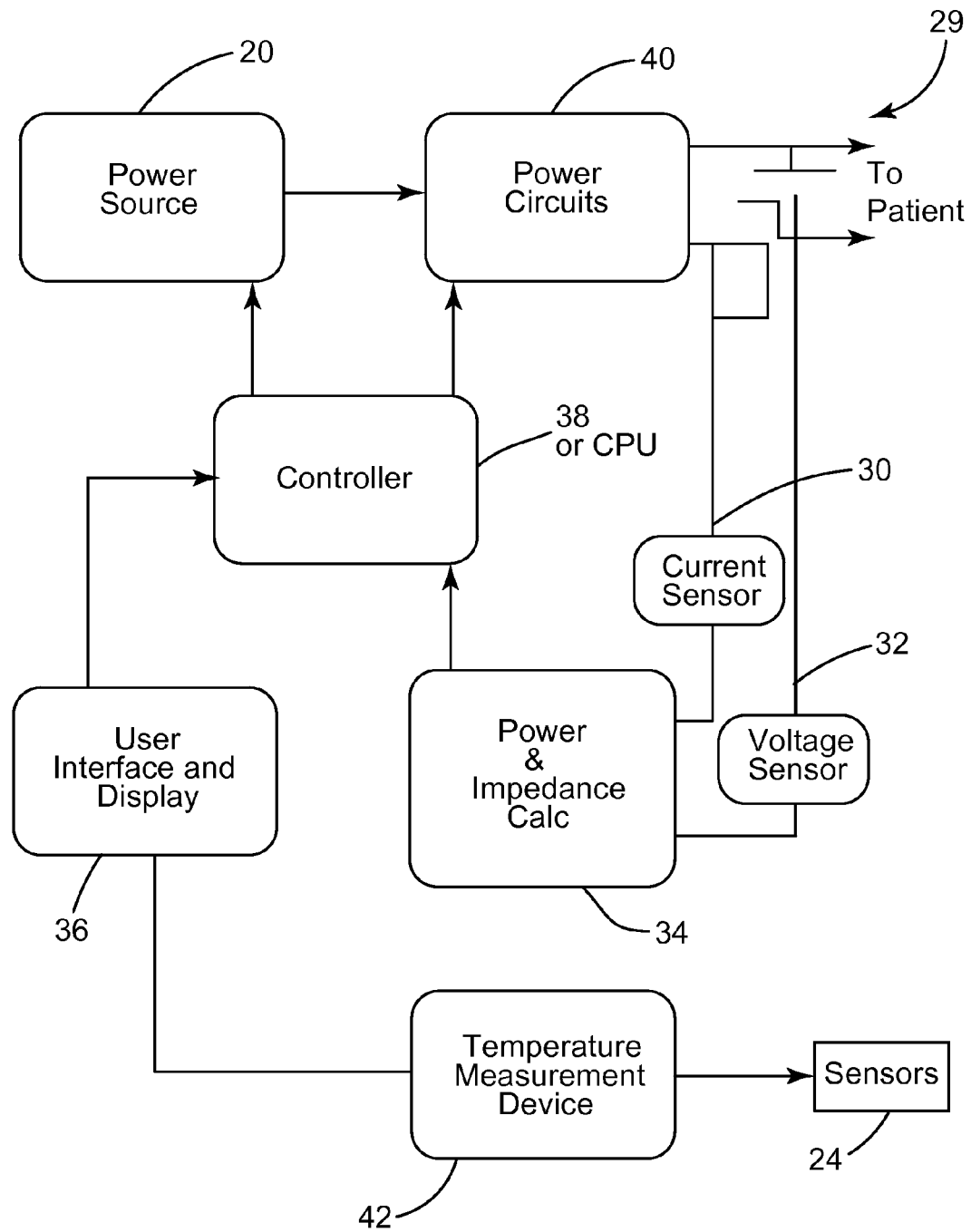
FIG. 9 is a block diagram illustrating the inclusion of a controller, energy source and other electronic components.

Referring now to FIGS. 1 and 9, a feedback control system 29 can be connected to energy source 20, sensors 24 and antennas 14 and 16. Feedback control system 29 receives temperature or impedance data from sensors 24, and the amount of electromagnetic energy delivered by antennas 14 and 16 is modified from an initial setting of ablation energy output, ablation time, temperature, and current density (the "Four Parameters"). Feedback control system 29 can automatically change any of the Four Parameters. Feedback control system 29 can detect impedance or temperature and change any of the Four Parameters. Feedback control system can include a multiplexer (not shown) to multiplex different antennas, a temperature detection circuit (as shown in FIG. 9) that provides a control signal representative of temperature or impedance detected at one or more sensors 24. A microprocessor can be connected to the temperature control circuit.

The following discussion pertains particularly to the use of an RF energy source and an RF multiple antenna device. It will be appreciated that devices similar to those associated with RF multiple antenna device can be utilized with laser optical fibers, microwave devices and the like.

Referring now to FIG. 9, all or portions of a feedback control system 29 are illustrated. Current delivered through primary and secondary antennas (not shown) to patient is measured by current sensor 30, while voltage is measured by voltage sensor 32. Impedance and power are then calculated by power and impedance calculation device 34. These values can then be displayed at user interface and display 36. Signals representative of power and impedance values are received by controller 38. A control signal is generated by controller 38 that is proportional to the difference between an actual measured impedance value and a desired impedance value. The control signal is used by power circuits 40 to adjust the power output in order to maintain the desired power delivered to patient through the primary and/or secondary antennas.

In a similar manner, temperatures detected at sensors 24 provide feedback to maintain a selected power output. The actual temperatures are measured at temperature measurement device 42, and the temperatures are displayed at user interface and display 36. A control signal is generated by controller 38 that is proportional to the difference between an actual measured temperature and a desired temperature. The control signal is used by power circuits 40 to adjust the power output in order to maintain the desired temperature at sensors 24. A multiplexer (not shown) can be included to measure current, voltage and temperature through current sensor 30, voltage sensor 32, and sensors 24, and energy is delivered to patient through the primary antenna and the secondary antennas.

Controller 38 can be a digital or analog controller, or a computer with software. When controller 38 is a computer, it can include a CPU coupled through a system bus. On this system can be a keyboard, a disk drive, or other non-volatile memory systems, a display, and other peripherals, as are known in the art. Also coupled to the bus include a program memory and a data memory.

User interface and display 36 includes operator controls and a display. Controller 38 can be coupled to imaging systems, including but not limited to ultrasound, CT scanners, X-ray, MRI, mammographic X-ray, and the like. Further, direct visualization and tactile imaging can be utilized.

The outputs of current sensor 30 and voltage sensor 32 are used by controller 38 to maintain a selected power output level to patient through primary and secondary antennas. The amount of RF energy delivered controls the amount of power output. A profile of energy delivered can be incorporated in controller 38, and a preset amount of energy to be delivered can also be profiled.

Circuitry, software and feedback to controller 38 result in process control and maintenance of the selected power output, and are used to change processes variables such as: (i) the selected power output, including RF, microwave, laser and the like, (ii) the duty cycle (on-off and wattage), (iii) bipolar or monopolar energy delivery, and (iv) infusion medium delivery, including flow rate and pressure. These process variables are controlled and varied, while maintaining the desired delivery of power output independent of changes in voltage or current, based on temperatures monitored at sensors 24.

Figure 10:
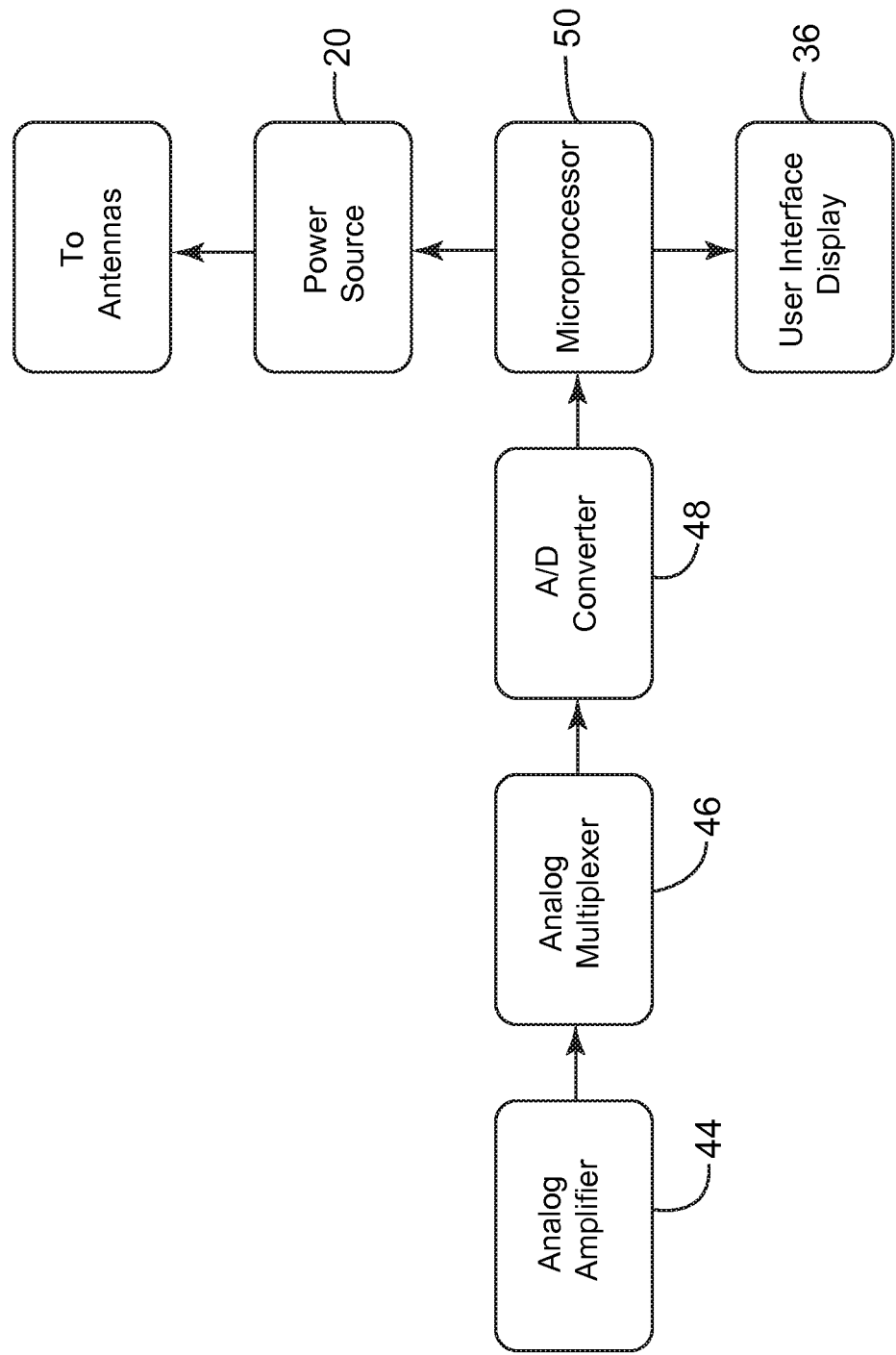
FIG. 10 is a block diagram illustrating an analog amplifier, analog multiplexer and microprocessor.

Referring now to FIGS. 9 and 10, current sensor 30 and voltage sensor 32 are connected to the input portion of an analog amplifier 44. Analog amplifier 44 can be a conventional differential amplifier circuit for use with sensors 24. The output portion of analog amplifier 44 is sequentially connected through an analog multiplexer 46 to the input portion of an A/D converter 48. The output of analog amplifier 44 is a voltage which represents the respective sensed temperatures at sensors 24. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by energy source 20 (shown in FIG. 1).

Figure 11:
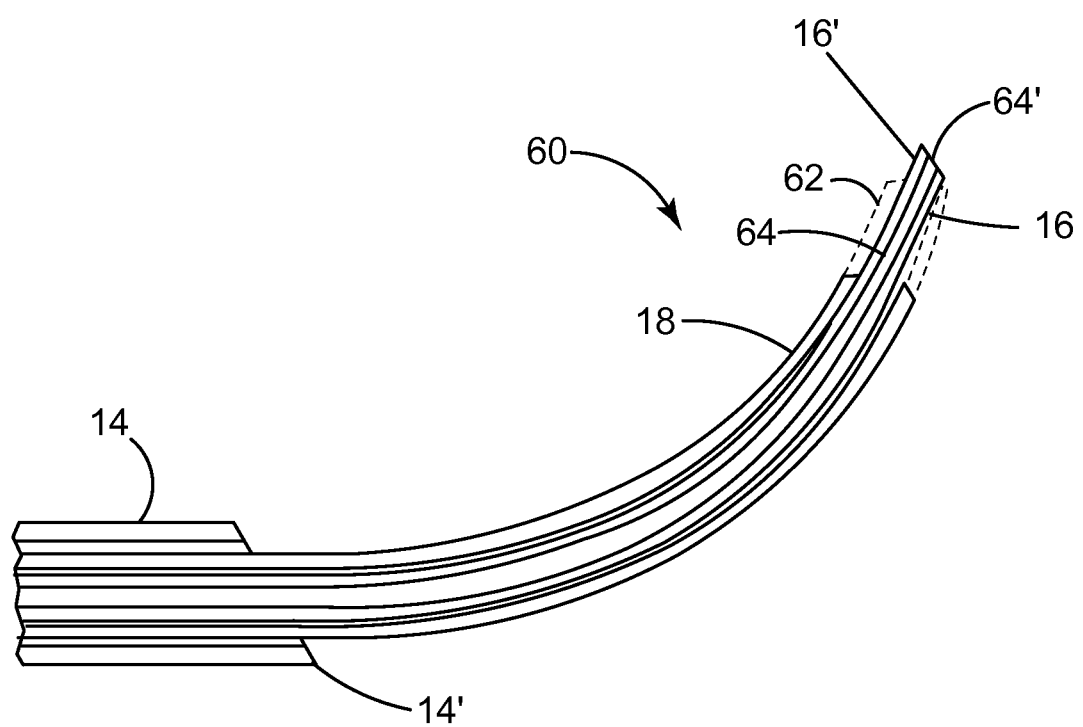
FIG. 11 is a fragmentary cross-sectional view of the tip of a stylet ablation device with the electrode and sleeve extended from the tip.

FIG. 11 is a cross-sectional view of the tip of a stylet ablation device with electrode 16 and sleeve 18 extended. This embodiment shows a flexible stylet 60 having a predetermined curved configuration. The flexible stylet can also be straight, if the remote position can be reached by a straight path from the point of entry without damaging a vital body component. Electrode 16 can be made of a shape memory alloy, shaped to revert to a desired configuration when deployed. The configuration can be simple curves, a combination of straight portions and curves, curves with different radii, in two or three dimensions, selected to direct electrode 16 and its surrounding, flexible, highly conformable sleeve 18 in a preselected two or three dimensional path through tissue to a site to be ablated.

Sleeve 18 is initially at the dotted line position 62. Following insertion into the body to the specific site to be ablated, sleeve 18 is withdrawn from a selected portion of electrode 16 to the solid line position to expose the specific electrode area required to form a lesion of a desired size.

When electrode 16 is a hollow tube, it can be a conduit for aspiration during treatment, liquid delivery, or in the embodiment shown, a housing for a fiber optic 64. The polished fiber optic tip 64' is then positioned behind electrode tip 16' to facilitate viewing of the tissue surrounding electrode tip 16'.

The foregoing description has been presented for purposes of illustration and description. It is not intended to be exhaustive or to limit the claimed invention to the precise forms disclosed. Obviously, many modifications and variations will be apparent to practitioners skilled in this art. It is intended that the scope of the claimed invention be defined by the following claims and their equivalents.

The invention claimed is:

1. A method of tissue treatment, comprising:
   providing an ablation device, wherein the ablation device comprises an introducer comprising a proximal portion and a distal portion; and at least one deployable means deployable from the introducer,
   wherein the at least one deployable means comprises at least one anchoring means;
   positioning the distal portion of the introducer within or adjacent to a selected tissue mass at a first position;
   deploying at least one of the anchoring means from the introducer to anchor the introducer relative to the selected tissue mass;
   delivering an ablation energy through at least one of the deployable means to treat a first volume of tissue;
   advancing at least one of the deployable means further in a distal direction to a second position within or adjacent to the selected tissue mass; and
   delivering the ablation energy through at least one of the deployable means at the second position to treat a second volume of tissue.

2. The method of claim 1, further comprising: delivering one or more of therapeutic agents, conductivity enhancement mediums, or infusion mediums to treat the selected tissue mass.

3. The method of claim 1, further comprising: delivering the ablation energy through at least one delivery surface of the at least one deployable means.

4. The method of claim 3, further comprising: adjusting the size or length of the at least one delivery surface.

5. The method of claim 1, further comprising: retracting the at least one deployable means.

6. The method of claim 1, further comprising: changing the delivery of the ablation energy between a monopolar mode and a bipolar mode.

7. The method of claim 1, further comprising: at least one of delivering the ablation energy in bipolar mode between two of the deployable means, and delivering the ablation energy in bipolar mode between the introducer and the at least one deployable means.

8. The method of claim 1, wherein at least one of the deployable means is configured to detect at least one of impedance and temperature.

9. The method of claim 1, wherein the ablation energy at both the first and second selected tissue sites is monopolar radiofrequency energy.

10. The method of claim 9, wherein the ablation energy at both the first and second selected tissue sites creates ionic agitation adjacent to the first and second selected tissue masses.

11. The method of claim 10, wherein the ionic agitation is proportional to the current density.

12. A method of tissue treatment, comprising:
   (a) providing an ablation device, wherein the ablation device comprises
      an introducer; and
      at least one deployable means deployable from the introducer, wherein the at least one deployable means comprises at least one anchoring means;
   (b) positioning a distal portion of the introducer within or adjacent to a selected tissue mass;
   (c) deploying the at least one anchoring means from the introducer to anchor the introducer relative to the selected tissue mass; and
   (d) delivering an ablation energy through at least one of the introducer and the deployable means to treat a volume of tissue;
   (e) advancing the at least one deployable means further in a distal direction to a second position within or adjacent to the selected tissue mass; and
   (f) delivering the ablation energy through the at least one deployable means at the second position to treat a second volume of tissue;
   (g) retracting at least one of the deployable means into the introducer.

13. The method of claim 12, further comprising; after step (d),
   delivering the ablation energy through at least one delivery surface of at least one of the introducer and the deployable means, and
   adjusting the size or length of the at least one delivery surface.

14. The method of claim 12, further comprising: delivering the ablation energy using a monopolar mode.

15. The method of claim 12, further comprising: at least one of delivering the ablation energy in bipolar mode between two of the deployable means, and delivering the ablation energy in bipolar mode between the introducer and the at least one deployable means.

16. The method of claim 12, further comprising: delivering one or more of therapeutic agents, conductivity enhancement mediums, or infusion mediums to treat the selected tissue mass.

17. The method of claim 12, wherein at least one of the deployable means is configured to detect at least one of impedance and temperature.

18. A method of tissue treatment, comprising:
   providing an ablation device, wherein the ablation device comprises an
      introducer; and
      at least one deployable means deployable from the introducer, wherein the at least one deployable means comprises at least one anchoring means;
   positioning a distal portion of the introducer within or adjacent to a selected tissue mass;
   deploying at least one of the deployable means from the introducer to a first position within or adjacent to the selected tissue mass;
   delivering an ablation energy through the at least one deployable means at the first position to treat a first volume of tissue, wherein the at least one deployed anchoring means forms a J hook geometric configuration;
   advancing the at least one deployable means further in a distal direction to a second position within or adjacent to the selected tissue mass; and
   delivering the ablation energy through the at least one deployable means at the second position to treat a second volume of tissue.

19. The method of claim 18, further comprising:
   delivering the ablation energy through at least one delivery surface of the at least one deployable means, and
   adjusting the size or length of the at least one delivery surface.

20. The method of claim 18, further comprising: changing the delivery of the ablation energy between a monopolar mode and a bipolar mode.

21. The method of claim 18, further comprising: at least one of delivering the ablation energy in bipolar mode between two of the deployable means, and delivering the ablation energy in bipolar mode between the introducer and the at least one deployable means, or both.

22. The method of claim 18, further comprising: delivering one or more of therapeutic agents, conductivity enhancement mediums, or infusion mediums to treat the selected tissue mass.

23. The method of claim 15, wherein at least one of the deployable means is configured to detect at least one of impedance and temperature.

24. A method of issue treatment, comprising:
- providing an ablation device, wherein the ablation device comprises an introducer, wherein the introducer comprises a proximal end, a distal end, and at least one aperture spaced proximally from the distal end; and
  - at least one deployable means deployable from the introducer, wherein the at least one deployable means comprises at least one anchoring means;
- positioning the distal end of the introducer within or adjacent to a selected tissue mass at a first position;
- delivering an ablation energy to at least one of the deployable means;
- deploying the at least one deployable means from the introducer through the at least one aperture; and
- advancing the at least one deployable means further a distal direction to a second position to create a series of ablations within or adjacent to the selected tissue mass.

* * * * *